United States Patent [19]  [11] 4,357,539
Fleer et al.  [45] Nov. 2, 1982

[54] FLEXIBLE FILM CASSETTE

[75] Inventors: Ernst O. Fleer; Werner Günther; Manfred Muether, all of Bensheim, Fed. Rep. of Germany

[73] Assignee: Siemens Aktiengesellschaft, Berlin & Munich, Fed. Rep. of Germany

[21] Appl. No.: 225,329

[22] Filed: Jan. 15, 1981

[30] Foreign Application Priority Data

Feb. 8, 1980 [DE] Fed. Rep. of Germany ....... 3004777

[51] Int. Cl.³ .......................... A61B 6/14; G03B 41/18
[52] U.S. Cl. ...................................... 378/170; 378/38; 378/169
[58] Field of Search ...................... 250/479, 439 P, 490

[56] References Cited

U.S. PATENT DOCUMENTS 2,829,263  4/1958  Butler .................................. 250/479
2,946,892  7/1960  Bas-Taymaz ........................ 250/479
4,104,531  8/1978  Weiss ................................. 250/439 P
4,104,532  8/1978  Weiss ................................. 250/439 P
4,193,002  7/1978  Muether et al. .................... 250/479

Primary Examiner—Alfred E. Smith
Assistant Examiner—T. N. Grigsby
Attorney, Agent, or Firm—Hill, Van Santen, Steadman, Chiara & Simpson

[57] ABSTRACT

A flexible film cassette for holding a dental x-ray film on the outside of a patient's mouth for exposure from a radiation source from an x-ray diagnostic installation or device in which an applicator is capable of being inserted intraorally in the patient's mouth characterized by a first support extending between an applicator and the cassette and a second support spaced an interval from the axis of the first support for forming a coupling between the film and the housing of the x-ray device to prevent rotation of the cassette relative to the applicator.

12 Claims, 2 Drawing Figures

FLEXIBLE FILM CASSETTE

BACKGROUND OF THE INVENTION

The present invention is directed to a flexible film cassette for supporting an x-ray film outside of a patient's mouth. The cassette is used with an x-ray diagnostic installation or device which has an x-ray tube which is mounted in a housing and has an applicator projecting from the housing which is capable of being inserted into the patient's mouth. The applicator and cassette have coacting means for supporting the cassette on the applicator.

A flexible film cassette, which is used with an x-ray diagnostic installation or device which has an x-ray tube which is supported in the housing and has an applicator protruding from the housing for insertion into the mouth of a patient, is disclosed in U.S. Pat. No. 4,193,002. In this patent, the cassette on a periphery has a supporting means which may either be a loop or a partial aperture for engaging a portion of the applicator and for positioning the cassette relative thereto.

With the provision of a support means for positioning the film cassette relative to the applicator which is inserted into the patient's mouth, it is possible to conduct either upper jaw or lower jaw radiographs from the standard radiograph as well as half side radiograph in a simple and time savings manner.

In order to achieve a good image quality, it is important that the focus of the radiation source, the radiation exit window of the applicator, the subject, and the x-ray film or the film cassette respectively are each in a position relative to one another which position is reproduceable to a great extent.

With known film cassettes, a good positioning of the film cassette on the applicator or on the patient's head is in deed possible. However, in the case of inexperienced handling, the attainment of the reproduceable radiograph with good image quality presents some problems.

SUMMARY OF THE INVENTION

The present invention is directed to providing an improved film cassette particularly in comparision with the above mentioned type of cassette which cassette enables obtaining an exact position of the film cassette relative to the application so that reproduceable radiographs with an improved image quality over the current obtainable radiographs can be made. In addition, the improved cassette enables the positioning of the cassette in an unmistakable fashion for use in either an upper jaw or lower jaw radiograph, as well as semi-lateral radiographs.

To accomplish these goals, the present invention is directed to an improvement in a flexible film cassette for receiving dental x-ray film and supporting the film on the outside of a patient's jaw, said cassette being used with an x-ray diagnostic installation or device which has an x-ray tube which is supported in a housing and an applicator projecting from the tube housing which is capable of being inserted into the patient's mouth, said film cassette on a periphery being provided with first support means at least partially surroundingthe applicator and forming a receiving opening for the mounting of the film cassette on the applicator. The improvement comprises second support means for positively coupling the cassette to the applicator being positioned at an interval from the center of the receiving opening of the first means, said second support means preventing rotation of the film cassette about the symmetrical axis of the applicator.

Through the proposed measures, an exact positioning of the film relative to the radiation exit window of the applicator is guaranteed. As a consequence of the twist proof positioning of the x-ray film on the applicator, a pivotable arrangement of the applicator is possible for alternate upper jaw and lower jaw radiographs with retention of the allocation of the x-ray film to the applicator.

An advantageous embodiment of the invention is that the second support means is designed in the form of a push button connection, wherein a projection or detent member coacts with a counter member or socket and these parts are effectively placed on only one side and as a consequence provide a clear positive coupling when the correct film position on the applicator occurs. The positive coupling can be designed differently in the case of different cassettes and applicators associated therewith, for example for a frontal radiograph and lateral radiograph. Thus, a push button pairing of the different sizes can be provided so that the cassette for one type is not mistakably used for a different type of radiograph. In order to guarantee a clear fixing of the correct film side on the applicator, only the side of the cassette facing the tube housing, i.e., the side opposite the patient's face, exhibits the support means which forms the coupling.

DESCRIPTION OF THE PREFERRED EMBODIMENTS

Figure 1:
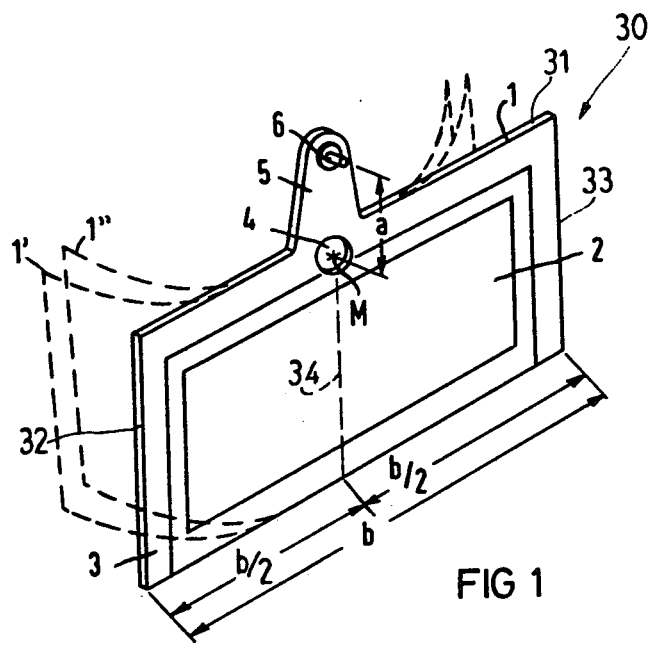
FIG. 1 is a perspective view of a flexible film cassette in accordance with the present invention.

The principles of the present invention are particularly useful in a flexible film cassette generally indicated at 30 in FIG. 1 which is employed in conjunction with a dental x-ray diagnostic installation or device which has an interoral x-ray tube.

The film cassette 30 essentially consists of a film pocket 1 in which an x-ray film 2 is mounted in the desired position. The film pocket 1, like the film itself, has a rectangular cross-section with a longitudinal side dimension b. Along its one long edge 31, and the short lateral edges 32 and 33 connected thereto by a 90°, the film pocket 1 contains reinforcement which enables a uniform bending through the positions 1' and 1" such as illustrated in broken lines and enable application or positioning the film cassette on the face of the patient. The reinforcements 3 moreover prevent to a satisfactory extent a so-called twisting of the film and increases its stability.

On a center line 34 of the cassette's major dimension b which center line is at a half width b/2 from either of the short edges 32 or 33, the cassette has an opening 4 which is adapted to receive an applicator such as 9 (FIG. 2) of an x-ray diagnostic device. Also, on the center line the cassette 30 has an integral tab 5 which is molded with the film pocket 1. The tab 5 at an interval or distance a from a center M of the receiving opening 4 is provided with a projection or detent member 6 which forms a part of a push button coupling that extends from one side of the cassette which is the side opposite that engaging the face of the patient. The projection or detent member 6 coacts with a corresponding design counter member or socket 7 (FIG. 2) which is arranged on a flange section 8 of the applicator 9. The distance a from the symmetrical axis 10 of the applicator 9 to the socket 7 corresponds to the distance a illustrated in FIG. 1.

Figure 2:
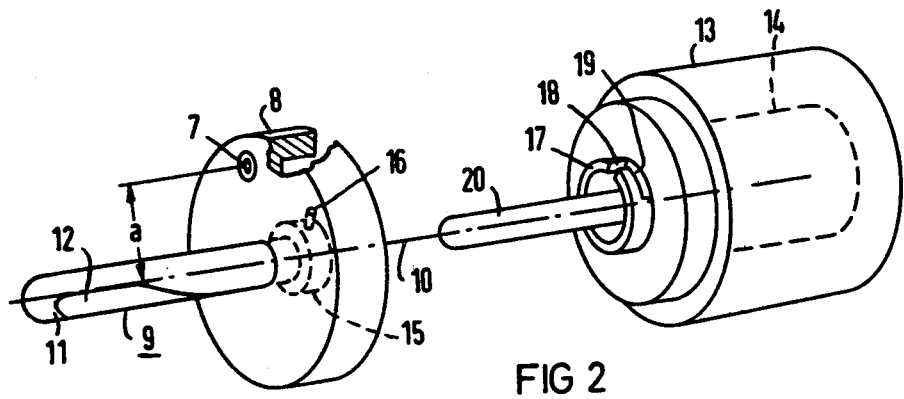
FIG. 2 is a perspective view of the x-ray diagnostic installation utilized with the cassette of FIG. 1 with the applicator being partially removed.

As best illustrated in FIG. 2, the applicator 9 contains a tubular section 11 which is closed on a front end. The tubular section 11 has an exit window 12 for the radiation generated by an anode tube 20 of an x-ray tube 14 which is arranged in a tube housing 13.

The applicator 9 is detachably mounted on the tube housing 13 with the aid of a bayonet connection consisting of a bolt or projection 16 mounted on a sleeve 15 and receivable in slots 18 and 19 which are provided on a flange 17 which is matched to telescopically receive the sleeve 15. In the assembled or connected state, the anode tube 20 which is connected to the x-ray tube 14 is inserted in the hollow cylindrical section 12 of the applicator 9. In the completely assembled state with the film cassette 30 placed on the applicator 9 and the coacting coupling parts 6 and 7 in engagement, the socket or counter part 7 is positioned so that the essentially longer side edges 31 having the length b is essentially a horizontal edge for the cassette.

To alternately make a radiograph of the lower jaw and upper jaw, an applicator must be either exchanged or replaced or must be rotated through 180°. To this end, additional slots would then be provided on the circumference of projection 17 and be identical to the slots 18 and 19 but positioned 180° from the slots 18 and 19.

Due to the first support mounting possibility of the film cassette created by the opening 4 receiving the applicator 9 and due to detachable mounting of the detent 6 is socket 7 which occurs at a distance from the opening 4 and which distance can be randomly selected, an exact positioning of the film relative to the radiation exit window 12 is thus guaranteed. In particular, the cassette is always aligned or directly oriented relative to the radiation exit window 12 and no twisting or rotating of the film cassette 30 is possible.

In order to obtain a clear allocation of the film cassette and the applicator to the desired radiograph type, i.e., a standard radiograph or a semilaterial radiograph, it is advantageous to provide the film cassette and respective applicator with differently designed and/or arranged support means respectively. Thus, the distance or interval a can have a different dimension in the case of a cassette for standard radiographs than for cassette for the semilateral radiograph. The size of the projection 6 and the socket 7 can be different so that a film cassette designed for standard radiograph cannot accidentally be used for a semilaterail radiograph.

Although various minor modifications may be suggested by those versed in the art, it should be understood that we wish to embody within the scope of the patent granted hereon, all such modifications as reasonably and properly come within the scope of our contribution to the art.

We claim:

1. In a flexible film cassette for receiving a dental x-ray film and supporting the film outside of a patient's mouth, said cassette being used with an x-ray diagnostic device which has an x-ray tube which is mounted in a housing and has an applicator projecting from the tube and the housing which is capable of being inserted into the patient's mouth, said film cassette on a periphery being provided with first support means at least partially surrounding the applicator and forming a receiving opening for the mounting of the film cassette on the applicator, the improvement comprising second support means for positively coupling the cassette to the applicator being positioned at an interval from the center of the receiving opening of the first support means, said second support means preventing rotation of the film cassette about the symmetrical axis of the applicator.

2. In a flexible film cassette according to claim 1, wherein the second support means comprises a coacting projection and a socket receiving said projection, said socket being disposed on the x-ray diagnostic installation and said projection being provided on the cassette.

3. In a flexible film cassette according to claim 2, wherein said cassette has a tab extending on a center line of the major axis of the cassette, said tab supporting said projection.

4. In a flexible film cassette according to claim 3, wherein the tab is integrally formed with the film cassette.

5. In a flexible film cassette according to claim 2, wherein the projection is disposed on a surface of the cassette opposite to the surface facing the patient's mouth.

6. In a flexible film cassette according to claim 1, wherein the second support means includes a push button coupling connection between said cassette and said x-ray diagnostic installation.

7. In a flexible film cassette according to claim 1, wherein the applicator adjacent the housing of the x-ray diagnostic device is provided with a flange, said second support means comprising a projection on said cassette and a socket disposed in said flange engaging said projection to form said coupling.

8. In a flexible film cassette according to claim 1, wherein said second support means includes a projection on one of said cassette and housing of the x-ray device, and a socket arranged on the other of the housing and cassette for receiving the projection, said device including at least one other projection and socket of a different size and interval for receiving a different cassette which is mounted in a different position.

9. In a flexible film cassette according to claim 1, wherein the cassette is directly mounted on the applicator, said applicator being mounted on the x-ray tube in at least two different positions about its axis of symmetry, one of said two positions having said applicator and cassette rotated through 180° on the axis of the applicator with respect to the other of said two positions.

10. In a flexible cassette according to claim 9, wherein the applicator is detachably mounted on the x-ray tube housing.

11. In a flexible cassette according to claim 1, wherein the cassette on each of its peripheral edges is provided with a flexible reinforcement so that the cassette is prevented from twisting.

12. In a cassette according to claim 1, wherein the second support means includes a projection received in a socket, said applicator having means for supporting one of said projection and sockets, said means for supporting being movable relatively around the axis of the applicator to enable positioning the cassette in more than one position.

* * * * *